(12) United States Patent
Fryer et al.

(10) Patent No.: US 6,491,881 B2
(45) Date of Patent: Dec. 10, 2002

(54) MONITORING OF STERILANT APPARATUS AND METHOD FOR MONITORING STERILANT

(75) Inventors: Ben Fryer, Lake Forest, CA (US); Debra Timm, Foothill Ranch, CA (US); Szu-Min Lin, Laguna Hills, CA (US); Henry Hui, Laguna Niguel, CA (US); Sam Nutt, Irvine, CA (US)

(73) Assignee: Ethicon, Inc., New Brunswick, NJ (US)

( * ) Notice: Subject to any disclaimer, the term of this patent is extended or adjusted under 35 U.S.C. 154(b) by 0 days.

(21) Appl. No.: 09/741,594

(22) Filed: Dec. 19, 2000

(65) Prior Publication Data

US 2001/0036670 A1 Nov. 1, 2001

Related U.S. Application Data

(63) Continuation-in-part of application No. 09/468,767, filed on Dec. 21, 1999.

(51) Int. Cl.$^7$ .............................................. A61L 2/20
(52) U.S. Cl. ............................ 422/292; 422/62; 422/3; 422/82.12; 436/1
(58) Field of Search ....................... 422/62, 292, 423, 422/82.12; 423/447.1; 607/96; 436/1

(56) References Cited

U.S. PATENT DOCUMENTS

| | | |
|---|---|---|
| 4,169,123 A | 9/1979 | Moore et al. |
| 4,169,124 A | 9/1979 | Forstrom et al. |
| 4,643,876 A | 2/1987 | Jacobs et al. |
| 4,756,882 A | 7/1988 | Jacobs et al. |
| 4,767,601 A | 8/1988 | Kuerzinger et al. |
| 4,783,317 A | 11/1988 | Kuerzinger et al. |
| 4,843,867 A | 7/1989 | Cummings |
| 5,167,927 A | 12/1992 | Karlson |
| 5,600,142 A | 2/1997 | Van Den Berg et al. |
| 5,608,156 A | 3/1997 | Ando et al. |
| 5,656,238 A | 8/1997 | Spencer et al. |
| 5,667,753 A | 9/1997 | Jacobs et al. |
| 5,780,715 A | 7/1998 | Imblum |
| 5,942,438 A | * 8/1999 | Antonoplos et al. ........... 436/1 |

FOREIGN PATENT DOCUMENTS

| | | | |
|---|---|---|---|
| DE | 42 12 910 A1 | | 10/1993 |
| EP | 0 178 507 A1 | | 4/1986 |
| EP | 0 262 670 A1 | | 6/1988 |
| GB | 2191585 A | * | 12/1987 |
| GB | 2 191 585 A | | 12/1987 |
| JP | 08038583 A | * | 2/1996 |
| JP | 01107120 A | * | 4/1999 |
| WO | WO-91/05998 | * | 5/1991 |

* cited by examiner

Primary Examiner—Robert J. Warden, Sr.
Assistant Examiner—Sean E. Conley
(74) Attorney, Agent, or Firm—Knobbe, Martens, Olson & Bear, LLP (57) ABSTRACT

An apparatus for monitoring the concentration of an oxidative gas or vapor includes a chemical substance which reacts with the oxidative gas or vapor to produce a heat change. A temperature probe is coupled to the chemical substance and adapted to respond to the heat change. The temperature probe can be coupled to the chemical substance by a carrier, and can include a reference temperature probe. Additionally, a method of using the apparatus is described, as well as a sterilization system which utilizes the apparatus.

31 Claims, 3 Drawing Sheets

MONITORING OF STERILANT APPARATUS AND METHOD FOR MONITORING STERILANT

CLAIM OF PRIORITY

This application is a continuation-in-part of, and claims priority from, U.S. Utility patent application Ser. No. 09/468,767 filed Dec. 21, 1999.

FIELD OF THE INVENTION

The invention relates to devices and techniques for monitoring the concentrations of an oxidative gas or vapor.

BACKGROUND OF THE INVENTION

Medical and surgical instruments have traditionally been sterilized using heat (e.g., exposure to steam), or chemical vapors (e.g., formaldehyde or ethylene oxide). However, both heat and chemical sterilizations have drawbacks. For example, many medical devices, such as fiberoptic devices, endoscopes, power tools, etc. are sensitive to heat, moisture, or both. Additionally, formaldehyde and ethylene oxide are both toxic gases which pose potential health risks to health workers. After sterilization with ethylene oxide, the sterilized articles require long aeration times to remove any remaining toxic material. This aeration step makes the sterilization cycle times undesirably long.

Sterilization using hydrogen peroxide vapor has been shown to have some advantages over other chemical sterilization processes (e.g., see U.S. Pat. Nos. 4,169,123 and 4,169,124). The combination of hydrogen peroxide vapor and a plasma provides additional advantages, as disclosed in U.S. Pat. No. 4,643,876. U.S. Pat. No. 4,756,882 discloses the use of hydrogen peroxide vapor, generated from an aqueous solution of hydrogen peroxide, as a precursor of the reactive species generated by a plasma. The combination of plasma and hydrogen peroxide vapor in close proximity with the sterilized articles acts to sterilize the articles.

Furthermore, use of low concentrations of hydrogen peroxide vapor has other advantages when used for chemical sterilization. Hydrogen peroxide is easy to handle, can be stored for long periods of time, is efficacious, and mixes readily with water. In addition, the products of decomposition of hydrogen peroxide are water and oxygen, which are both non-toxic.

However, there are problems with using hydrogen peroxide for sterilization. First, in order to be effective, devices must be exposed to a specified concentration of hydrogen peroxide. If the concentration of hydrogen peroxide is not sufficient, the article may require longer time and/or higher temperature to achieve sterilization. Second, if too much hydrogen peroxide is present, there is a risk of damaging the sterilized articles, particularly if they contain nylon, neoprene, or acrylic. For hydrogen peroxide absorbent materials, too much peroxide may leave an unacceptable residue on the sterilized article that may be incompatible with the user or patient. In addition, the use of too much hydrogen peroxide increases the cost of sterilization. Third, hydrogen peroxide concentration levels can decrease during the course of the sterilization process due to various factors, such as reactions with some surfaces which are undergoing sterilization, or permeation into and through some plastic materials. Fourth, hydrogen peroxide vapor can condense onto the walls of the sterilization chamber or onto equipment in the chamber, potentially degrading or harming the equipment. It is therefore important to be able to determine the concentration of hydrogen peroxide vapor in the sterilization chamber so that enough hydrogen peroxide is present to be effective, yet not so much that the sterilized articles or other equipment are damaged.

Furthermore, the concentration of hydrogen peroxide vapor can vary from one section of the sterilized articles to another. Even under equilibrium conditions, there may be regions of the sterilization chamber which are exposed to higher or lower concentrations of hydrogen peroxide due to restrictions of diffusion caused by other equipment in the chamber, or by the sterilized articles themselves. In particular, an enclosed volume with only a narrow opening will have a lower concentration of hydrogen peroxide than one with a wider opening. Under dynamic conditions (e.g., hydrogen peroxide is introduced into the chamber via an inlet port while at the same time, it is pumped out of an outlet port), the hydrogen peroxide concentration at a particular position in the chamber is a function of various factors, including the inlet flow, outlet pumping speed, and geometrical configuration of the system's inlet and outlet ports, sterilization chamber, and other equipment in the chamber, including the sterilized articles.

Various methods for determining hydrogen peroxide concentration levels in sterilization chambers have previously been disclosed. Ando et al. (U.S. Pat. No. 5,608,156) disclose using a semiconductor gas sensor as a means for measuring vapor phase hydrogen peroxide concentrations. The reaction time of the sensor is several tens of seconds, and the relation between the sensor output and the concentration of the hydrogen peroxide vapor varies with changes in pressure. Most hydrogen peroxide vapor sterilization procedures involve several treatment steps, usually including at least one step in vacuum. The response of the sensor to hydrogen peroxide through the treatment steps will therefore change, depending on the pressure used in each treatment step.

Cummings (U.S. Pat. No. 4,843,867) discloses a system for determining the concentration of hydrogen peroxide vapor in situ by simultaneous measurements of two separate properties, such as dew point and relative humidity. A microprocessor is then used to fit the two measurements into a model to calculate the hydrogen peroxide concentration. The method uses an indirect approximation based on a number of empirical assumptions, and the accuracy will vary depending on how closely the conditions in the sterilization chamber resemble those used to develop the model. This method also does not yield information concerning the differing concentrations of hydrogen peroxide at various positions within the sterilization chamber.

Van Den Berg et al. (U.S. Pat. No. 5,600,142) disclose a method of using near-infrared (NIR) spectroscopy to detect hydrogen peroxide vapor. Hydrogen peroxide has an absorption peak at about 1420 nm (nanometers) which can be used to determine its concentration. However, water is always present when hydrogen peroxide is present, since water is a decomposition product of hydrogen peroxide. Because water also absorbs near-infrared radiation at 1420 nm, it interferes with the determination of the hydrogen peroxide concentration. In order to correct for this interference, the water vapor concentration is determined separately by an absorption measurement at wavelengths which hydrogen peroxide does not absorb. This measured water vapor concentration is then used to correct the absorbance at 1420 nm for the contribution due to water. However, this correction measurement also suffers from contributions due to contaminants, such as various organic molecules, which absorb in the spectral region of the correction measurement.

Since one does not normally know what organic molecules are present, the correction factor is therefore somewhat unreliable.

Furthermore, the NIR method requires absorption measurements at two different wavelengths and making corrections for the presence of water vapor, organic contaminants, or both. The electronic equipment for doing these corrections is complex and expensive, and the correction for the presence of organic compounds is subject to error. Additionally, the calculated hydrogen peroxide concentration is an average concentration over the volume which absorbs the near-infrared radiation, not a localized measurement of concentration at particular positions within the sterilization chamber.

U.S. Pat. No. 4,783,317 discloses an apparatus for monitoring the concentration of hydrogen peroxide in liquid media, e.g. aqueous solutions for scrubbing the flue gases emanating from waste-incineration plants or large capacity firing systems. By exploiting the exothermic reaction of hydrogen peroxide with reducing agents (e.g. gaseous sulfur dioxide), the apparatus is able to measure the concentration of hydrogen peroxide in the liquid medium. The U-shaped apparatus comprises a thermally insulated measuring cell, a supply line which supplies a partial stream of the liquid from the source to the measuring cell, and a discharge line which returns the liquid to the source. In the measuring cell, the liquid is combined with a small stream of a reducing agent from a separate supply line, and the temperature of the mixture is monitored by a sensor. By comparing this temperature to the temperature of the liquid prior to entering the measuring cell, the apparatus measures temperature rise due to the ongoing exothermic reaction which is a function of the concentration of hydrogen peroxide in the liquid.

SUMMARY OF THE INVENTION

In one aspect, the present invention provides an apparatus for monitoring the concentration of an oxidative gas or vapor, the apparatus comprising a chemical substance which reacts with the oxidative gas or vapor to produce a heat change. The apparatus further comprises a temperature probe coupled to the chemical substance and adapted to respond to the heat change.

In another aspect, the present invention provides a method of monitoring the concentration of an oxidative gas or vapor, the method comprising providing a chemical substance which undergoes a reaction with the oxidative gas or vapor to be monitored, thereby producing a heat change. The method further comprises providing a temperature probe coupled to the chemical substance, the temperature probe responding to the heat change produced by the reaction between the chemical substance and the oxidative gas or vapor to be monitored by producing an output signal which is a function of the concentration of the oxidative gas or vapor. The chemical substance coupled to the temperature probe is exposed to the oxidative gas or vapor, the output signal from the temperature probe is measured, and the concentration of the oxidative gas or vapor is determined based on the output signal.

In still another aspect, the apparatus described above can form part of a sterilization system operated by a user. The sterilization system comprises a chamber, a door in the chamber, and a source of oxidative gas or vapor in fluid connection with the chamber. The sterilization system further comprises a chemical concentration measuring system comprising at least one apparatus for monitoring the concentration of an oxidative gas or vapor. A control system receives input from the chemical concentration measuring system to produce a desired concentration of said oxidative gas or vapor.

DETAILED DESCRIPTION OF THE PREFERRED EMBODIMENT

FIGS. 1A, 1B, 1C, 1D, and 1E illustrate embodiments of the present invention. In a preferred embodiment of the present invention, a concentration monitor 10 comprises a carrier 12, a chemical substance 14, and a temperature probe 16. All of the elements of the concentration monitor 10 must be compatible with its operating conditions. Concentration monitors 10 compatible with the present invention can operate under a wide range of pressures, such as atmospheric pressures or sub-atmospheric pressures (i.e., vacuum pressures). For use in a sterilization system utilizing hydrogen peroxide vapor with or without plasma, the carrier 12, chemical substance 14, and temperature probe 16 must all be compatible with operations under sterilization conditions and with exposure to hydrogen peroxide vapor and plasma. Persons skilled in the art recognize that there is a wide variety of materials and structures which can be selected as the carrier 12 in these preferred embodiments. The carrier 12 couples the chemical substance 14 in close proximity to the temperature probe 16 so as to minimize the thermal losses between them. Examples of adequate carriers include, but are not limited to, acrylic, epoxy, nylons, polyurethane, polyhydroxy-ethylenemethacrylate (polyHEMA), polymethylmethacrylate (PMMA), polyvinyl-pyrrolidone (PVP), polyvinylalcohol (PVA), silicone, tape, or vacuum grease. Additionally, the carrier 12 can either be configured to expose the chemical substance 14 directly to the environment, or to enclose the chemical substance 14 in a gas permeable pouch, such as Tyvek tubing, or a gas impermeable enclosure with a hole or holes. In certain embodiments, the chemical substance 14 can be coupled directly to the temperature probe 16 without use of a carrier. For example, the chemical substance 14 can be formed as an integral part of the temperature probe 16 or, if the chemical substance 14 is sufficiently adhesive, it can be directly coupled to the temperature probe 16.

The chemical substance 14 undergoes an exothermic reaction with the oxidative gas or vapor to be monitored, producing a detectable amount of thermal energy (i.e., heat) upon exposure to the oxidative gas or vapor to be monitored. Persons skilled in the art are able to choose an appropriate chemical substance 14 which yields a sufficient amount of heat upon exposure to the relevant range of concentrations of the oxidative gas or vapor to be measured. Examples of chemical substances 14 for use in a hydrogen peroxide sterilization system include, but are not limited to, substances that catalytically decompose hydrogen peroxide, substances that are easily oxidized by hydrogen peroxide, and substances that contain hydroxyl functional groups. Substances that catalytically decompose hydrogen peroxide include, but are not limited to, catalase, copper and copper alloys, iron, silver, platinum, and platinum on alumina. Substances that are easily oxidized by hydrogen peroxide include, but are not limited to, magnesium chloride ($MgCl_2$), iron (II) compounds such as iron (II) acetate, potassium iodide (KI), sodium thiosulfate, and sulfides and disulfides such as molybdenum disulfide, 1,2-ethanedithiol, methyl disulfide, cysteine, methionine, and polysulfides. Substances that contain hydroxyl functional groups include, but are not limited to, polyethylene glycol (PEG), polyethylene oxide (PEO), and polyvinyl alcohol (PVA). These substances can be in the form of polymers that comprise hydroxyl functional groups, and persons skilled in the art appreciate that such polymers can also be co-polymers. In addition, a combination of these above-described substances may be chosen as the chemical substance 14. Furthermore, persons skilled in the art are able to select the appropriate amount of chemical substance 14 to yield a sufficient amount of heat upon exposure to the relevant range of hydrogen peroxide concentrations.

Figure 1A:
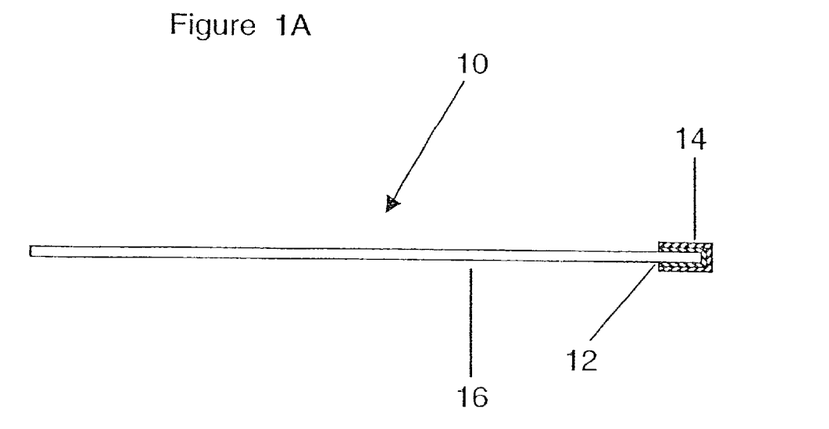
FIGS. 1A 1B, 1C, 1D, and 1E schematically illustrate various preferred embodiments of the present invention comprising a carrier, a chemical substance, and a temperature probe.
Figure 1B:
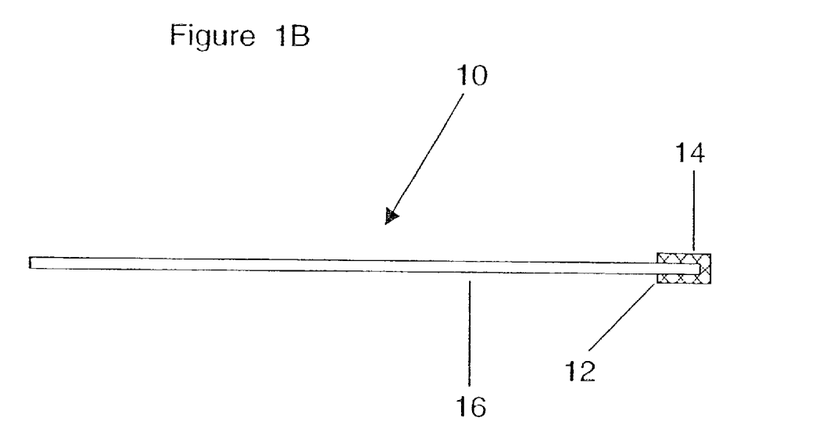
Figure 1C:
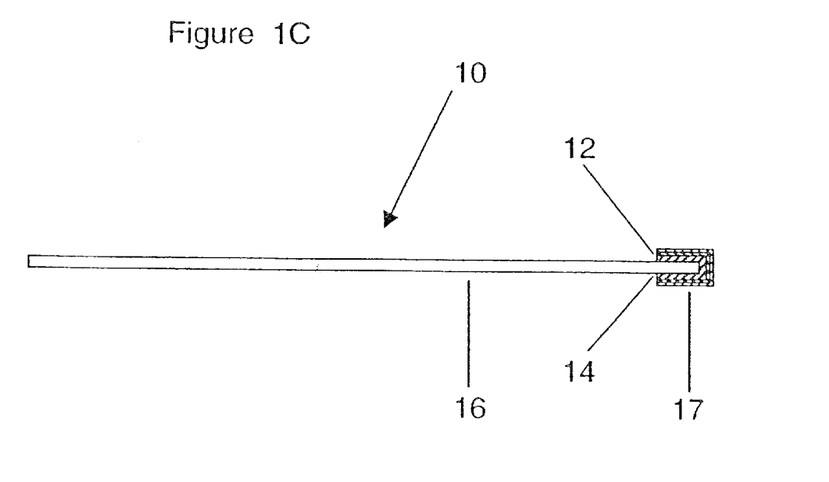
Figure 1D:
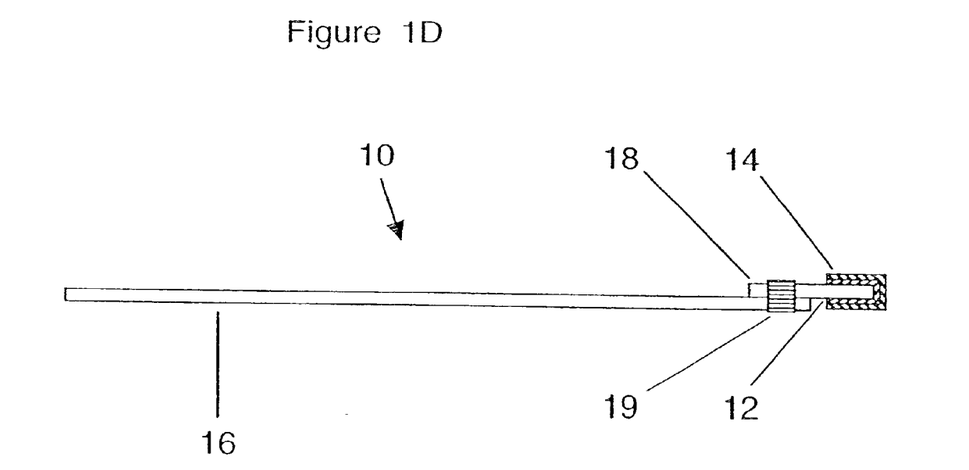
Figure 1E:
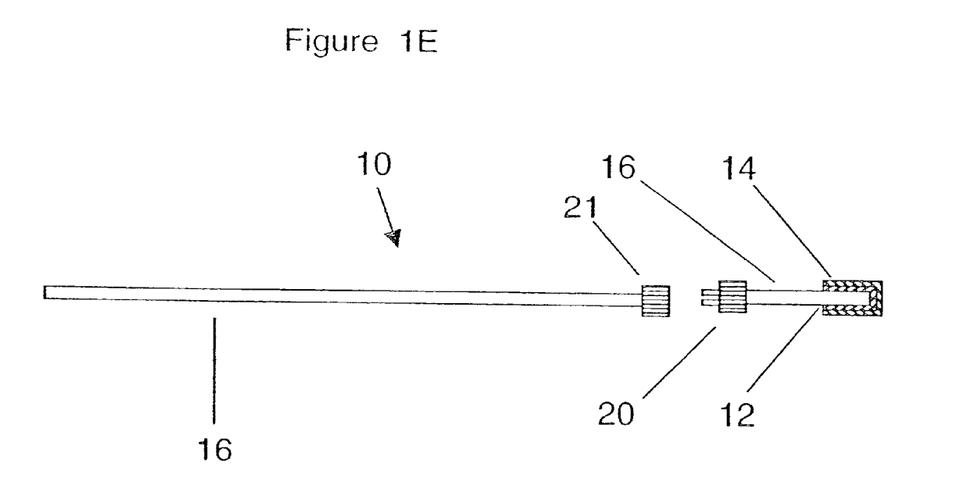

Various configurations are compatible with use in the preferred embodiments illustrated in FIGS. 1A, 1B, 1C, 1D, and 1E. FIG. 1A shows a temperature probe 16 coated with a thin layer of carrier 12 on the tip of the probe 16 and the chemical substance 14 is coated on the outside of the carrier 12. FIG. 1B shows the chemical substance 14 is mixed with the carrier 12 and applied onto the tip of the temperature probe 16. For example, a chemical substance 14 such as PEG is mixed with a carrier 12 such as acrylic binder in an aqueous suspension, then coated onto a temperature probe 16. The chemical substance 14 is accessible for reaction as the hydrogen peroxide diffuses into the carrier. FIG. 1C show the chemical substance 14 is enclosed onto the tip of the temperature probe 16 with a carrier 12. The carrier 12 is a gas-permeable pouch with a heat-sealed area 17, which typically is composed of a nonwoven polyolefin material, such as Tyvek® (nonwoven polyethelene) sold by E.I. du Pont de Nemours and Co. of Wilmington, Del. or CSR (central supply room) wrapping material (nonwoven polypropylene) sold by Kimberly-Clark Corp. of Dallas, Tex. The carrier 12 can also be a gas-impermeable pouch or other enclosure with one or more holes to allow the diffusion of gas or vapor to react with the chemical substance 14 retained in the enclosure. FIG. 1D shows a chemical substance 14 coupled to a heat-conducting material 18 with a carrier 12, and the heat-conducting material 18 is coupled to the temperature probe 16 with a substrate 19. The substrate 19 can be tape, adhesive, or any other coupling means. The heat-conducting material 18 can be metallic wire or any other materials which can properly conduct heat to the temperature probe 16. FIG. 1E show a chemical substance 14 coupled to a temperature probe 16 with a carrier 12, and two parts of the temperature probe 16 can be connected and disconnected with a male connector 20 and a female connector 21.

The temperature probe 16 is a device which measures the temperature at a particular location. One embodiment of the present invention utilizes a fiberoptic temperature probe, such as a Luxtron 3100 fluoroptic thermometer, as the temperature probe 16. This fiberoptic temperature probe 16 is coated with Teflon and therefore is very compatible to any oxidative gas or vapor. Another embodiment utilizes a temperature probe 16 which is a thermocouple probe which utilizes a junction of two metals or alloys. The thermocouple junction produces a voltage which is a known function of the junction's temperature. Measurements of this voltage across the thermocouple junction can therefore be converted into measurements of the junction's temperature. Thermocouple junctions can be made quite small (e.g., by spot welding together two wires of 0.025-millimeter diameter composed of differing alloys), so they can be positioned into size-restricted volumes. In yet other embodiments, the temperature probe 16 can be a thermistor, glass thermometer, RTD probe, temperature strip, optical temperature sensor, or infrared temperature sensor.

Table 1 illustrates the increases of temperature measured by a concentration monitor 10 with potassium iodide (KI) as the chemical substance 14. The tip of the fiberoptic temperature probe was first coated with a thin layer of Dow Coming high vacuum grease (part number 2021846-0888). About 0.15 grams of KI powder was then applied onto the vacuum grease. This configuration is the same as illustrated in FIG. 1A. The measurements were conducted by suspending the concentration monitor 10 in a vacuum chamber heated to 45° C., evacuating the chamber, recording the initial probe temperature, injecting hydrogen peroxide into the chamber, recording the temperature after all hydrogen peroxide was vaporized, evacuating the chamber to remove the hydrogen peroxide, and venting the chamber. The measurements were repeated with different concentrations of hydrogen peroxide injected into the chamber. The same temperature probe 16 was reused for all the measurements, and the results are shown in Table 1. As can be seen from Table 1, KI produces a measurable increase of temperature with increasing concentration of hydrogen peroxide. Additionally, this concentration monitor 10 can be reused many times.

TABLE 1

| Concentration of $H_2O_2$ (mg/L) | Temperature increase (° C.) |
|---|---|
| 0.2 | 3.0 |
| 0.4 | 8.3 |
| 0.8 | 19.2 |
| 1.3 | 24.2 |
| 2.1 | 33.7 |

Table 2 provides data on the measured temperature increases with varying concentrations of hydrogen peroxide for a concentration monitor 10 utilizing different chemical substances 14. Same test conditions and probe configurations were used in these temperature measurements. As can be seen from Table 2, each of the chemical substances 14 produced a measurable temperature rise which increased with increasing hydrogen peroxide concentration.

TABLE 2

| | Temperature increase (° C.) | | |
|---|---|---|---|
| Chemical substance | 0.4 mg/L | 1.0 mg/L | 2.1 mg/L |
| Platinum on Alumina | 13.5 | 17.2 | — |
| Catalase | 1.1 | — | 6.9 |
| Iron (II) acetate | 62.5 | 83.1 | — |
| Magnesium Chloride | 0.8 | — | 4.4 |

The utility of using a thermocouple junction as the temperature probe 16 is illustrated in Table 3. For these measurements, the concentration monitor 10 was configured as illustrated in FIG. 1A. The test conditions of Table 1 were also used for these measurements. Table 3 illustrates that significant temperature increases were also observed using a thermocouple temperature probe 16.

TABLE 3

| Concentration of $H_2O_2$ (mg/L) | Temperature increase (° C.) |
|---|---|
| 0.2 | 2.7 |
| 0.4 | 11.9 |
| 0.8 | 19.3 |
| 2.1 | 24.2 |

The utility of using double-sided tape as the carrier 12 is illustrated by Table 4, which presents the temperature increases measured by a fiberoptic temperature probe 16. A thin layer of 3M Scotch double-sided tape was first applied to the tip of the fiberoptic probe 16. About 0.15 grams of KI powder was then coated onto the tape. Table 1 test conditions were repeated for these measurements. It is apparent from Table 4 that measurable increases of temperature were detected for increasing $H_2O_2$ concentration when using double-sided tape as the carrier 12.

TABLE 4

| Concentration of $H_2O_2$ (mg/L) | Temperature increase (° C.) |
|---|---|
| 0.4 | 9.3 |
| 1 | 16.8 |
| 2.1 | 31.2 |

The utility of using epoxy as the carrier 12 is illustrated by Table 5, which presents the temperature increases measured by a fiberoptic temperature probe 16. The concentration monitor 10 was constructed by applying a thin layer of Cole-Palmer 8778 epoxy on an aluminum wire. About 0.15 grams of KI powder was then applied and dried onto the epoxy. Finally, the aluminum wire was attached to the temperature probe 16. Table 1 test conditions were repeated for these measurements. It is apparent that measurable increases of temperature were detected for increasing $H_2O_2$ concentration when using epoxy as the carrier 12.

TABLE 5

| Concentration of $H_2O_2$ (mg/L) | Temperature increase (° C.) |
|---|---|
| 0.4 | 7.8 |
| 1 | 12.9 |
| 2.1 | 20.1 |

The utility of using an enclosure as the carrier 12 to enclose the chemical substance 14 is illustrated by Tables 6 and 7, which illustrate the increase of temperature detected by a fiberoptic temperature probe 16 with KI contained in an enclosure. For Table 6, the enclosure was PVC shrink tubing with holes. The holes were small enough to trap the KI powder but large enough to allow the diffusion of gas or vapor into the PVC tubing. For Table 7, the enclosure was gas-permeable Tyvek tubing fabricated from heat-sealed 1073B Tyvek. The inner diameter of the enclosure was about 0.5 centimeters, and its length was approximately 1.5 centimeters. For Table 6, about 0.2 grams of KI powder was enclosed in the PVC tubing and the concentration monitor 10 was re-used for all measurements. For Table 7, about 0.2 grams of KI powder was enclosed in the Tyvek pouch and the concentration monitor 10 was also re-used for all measurements. Table 1 test conditions were used for these measurements. It is apparent that measurable increases of temperature were detected for increasing $H_2O_2$ concentration when using both embodiments of a gas-permeable pouch as the carrier 12. The results also demonstrate that the concentration monitor 10 can be re-used and the measurements are reproducible.

TABLE 6

| Concentration of | Temperature increase (° C.) | | |
|---|---|---|---|
| $H_2O_2$ (mg/L) | Trial #1 | Trial #2 | Average |
| 0.2 | 1.1 | 1.1 | 1.1 |
| 0.4 | 9.5 | 8.8 | 9.2 |
| 1.0 | 13.6 | 13.6 | 13.6 |

TABLE 7

| Concentration of | Temperature increase (° C.) | | |
|---|---|---|---|
| $H_2O_2$ (mg/L) | Trial #1 | Trial #2 | Average |
| 0.4 | 9.7 | 8.4 | 9.1 |
| 1.0 | 17.3 | 16.8 | 17.1 |
| 1.4 | 23.6 | 23.6 | 23.6 |

A chemical substance 14 comprising a polymer comprising hydroxyl functional groups may also be used to fabricate a hydrogen peroxide monitor. For example, polyethylene glycol or PEG, with a formulation of $H(OCH_2CH_2)_nOH$, mixed with an acrylic binder in aqueous suspension provides a hydrogen peroxide monitor compatible with the present invention. Such chemical substances have a high specificity to oxidative gas or vapor, such as $H_2O_2$, and essentially no sensitivity to $H_2O$. Persons skilled in the art appreciate that other polymers containing hydroxyl functional groups are also compatible with the present invention.

To examine the utility of a PEG/acrylic suspension, various $H_2O_2$ monitors were fabricated using the following procedure. A 1:1 ratio by weight PEG/acrylic mixture was made by mixing and stirring 5 g of acrylic binder (Vivitone, Inc., product number 37-14125-001, metallic binder LNG) with 5 g of PEG (Aldrich, Inc., product number 30902-8, molecular weight of approximately 10,000) in a 20-g scintillation vial. Other embodiments compatible with the present invention can utilize ratios other than 1:1. The mixture was then heated to approximately 75° C. and stirred thoroughly. After allowing the mixture to cool to room temperature, the vial containing the suspension was capped and stored in a cool, dark environment.

To fabricate each $H_2O_2$ monitor, the metal surface of a thermocouple was chemically treated to improve the adhesion of the chemical substance 14 to the carrier 12. The thermocouple was soaked in isopropyl alcohol for approximately two minutes and its end was brushed lightly to remove debris. After air-drying for approximately five minutes, the end of the thermocouple was soaked in approximately 10–20% by volume sulfuric acid ($H_2SO_4$) for approximately two minutes, then rinsed thoroughly in generous amounts of deionized water. The thermocouple was then dried in an oven at approximately 55° C. for approximately five minutes, then allowed to cool to room temperature outside the oven for approximately five minutes. The end of the thermocouple was then coated with the PEG/acrylic mixture by dipping the end of the thermocouple into the vial containing the mixture. Note that in order to produce a thicker overall coating, the end of the thermocouple can be dipped repeatedly. The thermocouple was then returned to the oven to dry at approximately 55° C. for approximately five minutes. A similar procedure was used to fabricate PEO/acrylic $H_2O_2$ monitors.

The above procedure can generate $H_2O_2$ monitors which are durable, inexpensive, and easy to manufacture. Also, PEG/acrylic mixtures have a relatively long shelf life of more than approximately three years. By utilizing a coating of the PEG/acrylic suspension, very small and flexible $H_2O_2$ monitors can be fabricated with different sizes and shapes. For example, if it is desirable to measure the $H_2O_2$ concentration within a narrow tube, the reactive chemical substance can be coated onto an optical fiber such as a Luxtron® fluoroptic temperature probe, a fiberoptic temperature probe, or on a metal wire of a thermister or thermocouple assembly.

PEG/acrylic $H_2O_2$ monitors and PEO/acrylic $H_2O_2$ monitors fabricated by the above procedure were tested in a STERRAD® 100 low temperature, hydrogen peroxide gas plasma sterilization system. The sensitivity of these $H_2O_2$ monitors to hydrogen peroxide vapor is illustrated in Table 8 which provides the measured temperature increases in ° C. generated by the $H_2O_2$ monitors for different concentrations of $H_2O_2$ in the STERRAD® chamber. The change of temperature is referenced to the temperature read by the thermocouple just prior to the injection of $H_2O_2$.

TABLE 8

| $H_2O_2$ (mg/L) | Temperature Increase (° C.) | |
| --- | --- | --- |
| | PEG/acrylic | PEO/acrylic |
| 0.41 | 2.6 | 2.0 |
| 0.77 | 3.4 | 3.5 |
| 1.45 | 5.8 | 5.6 |
| 2.87 | 9.4 | 9.7 |
| 5.73 | 16.1 | 14.0 |
| 11.5 | 24.2 | 22.0 |

Measured temperature increases for known $H_2O_2$ concentrations can be used to generate a calibration curve for such $H_2O_2$ monitors. The $H_2O_2$ responses of individual $H_2O_2$ monitors using the same chemical substance/carrier mixture were substantially similar to one another, indicating that $H_2O_2$ monitors with reproducible responses to $H_2O_2$ can be produced. For sufficient reproducibility among the $H_2O_2$ monitors using the same chemical substance/carrier mixture, a standard response equation can express the response for all such $H_2O_2$ monitors, thereby eliminating the need for individual calibration of the $H_2O_2$ monitors to convert the temperature change into a measurement of the $H_2O_2$ concentration.

$H_2O_2$ monitors compatible with the present invention with a reactive chemical substance/carrier such as the PEG/acrylic mixture can utilize other temperature probes 16 besides thermocouples. Appropriate temperature probes 16 include, but are not limited to, glass thermometers, thermocouples, thermisters, RTD probes, temperature strips, optical temperature sensors, and infrared temperature sensors. In addition, the sensing surface of the temperature probe 16 can be chemically or mechanically etched to improve the adhesion between the reactive chemical substance 14 and the temperature probe 16. The reactive chemical substance 14 can be coated onto the temperature sensitive surface of the temperature probe 16 by a variety of methods, including but not limited to, dipping, painting, or spraying. For faster response times, it is preferable to apply a thin coat of the reactive chemical substance 14 on the temperature probe 16. The thickness of the coating can also be controlled by adjusting the speed of withdrawl of the probe 16 from the solution as it is being coated, and the viscosity of the reactive chemical substance 14. Additional layers of the reactive chemical substance 14 can be added to the initial coating to improve signal strength and/or sensitivity.

Figure 2:
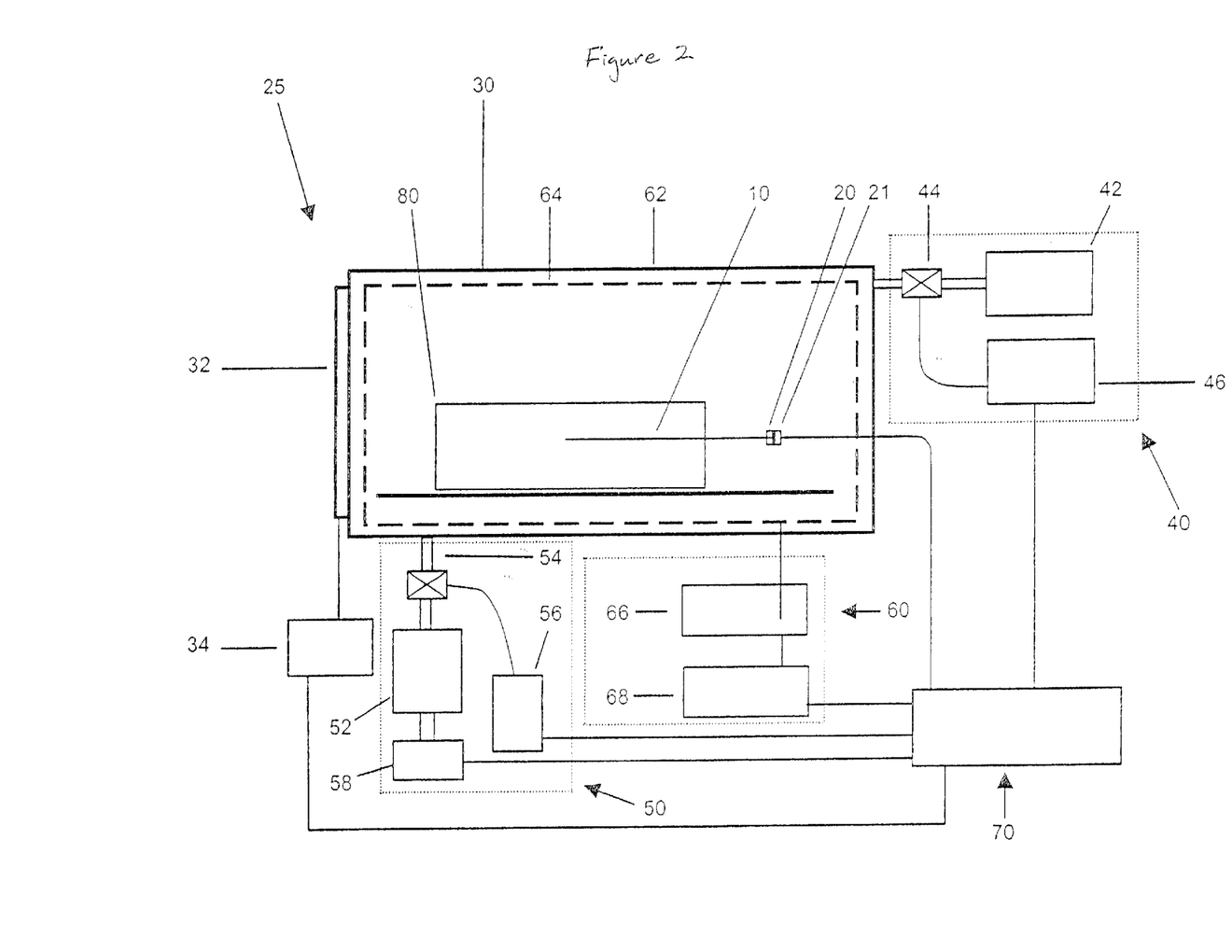
FIG. 2 schematically illustrates a sterilization system utilizing one preferred embodiment of the present invention.

FIG. 2 schematically illustrates a sterilization system 25 utilizing one preferred embodiment of the present invention. The sterilization system 25 has a vacuum chamber 30 with a door 32 through which items to be sterilized are entered into and removed from the chamber 30. The door is operated by utilizing a door controller 34. The vacuum chamber 30 also has a gas inlet system 40, a gas outlet system 50, and a radio-frequency (rf) system 60. Other embodiments compatible with the present invention can utilize a low frequency plasma sterilization system, such as that described in "Sterilization System Employing Low Frequency Plasma", U.S. patent application Ser. No. 09/676,919, which is incorporated by reference herein. Comprising the gas inlet system 40 is a source of hydrogen peroxide ($H_2O_2$) 42, a valve 44, and a valve controller 46. The gas outlet system 50 comprises a vacuum pumping system 52, a valve 54, a valve controller 56, and a vacuum pumping system controller 58. In order to apply radio-frequency energy to the $H_2O_2$ in the vacuum chamber 30, the rf system 60 comprises a ground electrode 62, a powered electrode 64, a power source 66, and a power controller 68. The sterilization system 25 is operated by utilizing a control system 70 which receives input from the operator, and sends signals to the door controller 34, valve controllers 46 and 56, vacuum pumping system controller 58, and power controller 68. Coupled to the control system 70 (e.g., a microprocessor) is the concentration monitor 10, which sends signals to the control system 70 which are converted into information about the $H_2O_2$ concentration in the vacuum chamber 30 at the location of the concentration monitor 10. The sterilized article 80 is shown to be positioned in the chamber 30 with concentration monitor 10 located in the load region to monitor the concentration of hydrogen peroxide in the load region. Persons skilled in the art are able to select the appropriate devices to adequately practice the present invention.

The heat produced between the oxidative gas or vapor and the chemical substance 14 may not be the same for different configurations of the concentration monitor 10, carrier 12, and chemical substance 14. Therefore, for a given type of concentration monitor 10, a calibration curve needs to be established to determine the relationship between the concentration of oxidative gas or vapor and the heat produced. Once the calibration curve is established, the heat detected during the measurement can be converted to the concentration of the oxidative gas or vapor around the monitor 10.

By coupling the operation of the sterilization system 25 with the $H_2O_2$ concentration measured by the concentration monitor 10, the sterilization system 25 is assured of operating with an appropriate amount of $H_2O_2$ in the region of the articles to be sterilized. First, if the $H_2O_2$ concentration is determined to be too low for adequate sterilization, the control system 70 can signal the inlet valve controller 46 to open the inlet valve 44, thereby permitting more $H_2O_2$ into the chamber 30. Alternatively, if the $H_2O_2$ concentration is determined to be too high, the control system 70 can signal the outlet valve controller 56 to open the outlet valve 54, thereby permitting the vacuum pumping system 52 to remove some $H_2O_2$ from the chamber 30. Furthermore, if the sterilization system is being operated in a dynamic pumping mode (i.e., $H_2O_2$ is introduced into the chamber 30 via the inlet valve 44 while at the same time, it is pumped out via the outlet valve 54), then either the inlet valve 44 or the outlet valve 54, or both can be adjusted in response to the measured $H_2O_2$ concentration to ensure an appropriate level of $H_2O_2$.

Because the concentration monitor 10 provides localized information regarding the $H_2O_2$ concentration, it is important to correctly position the concentration monitor 10 within the sterilization chamber 30. In some preferred embodiments, the concentration monitor 10 is fixed to a particular position within the sterilization chamber 30 in proximity to the position of the sterilized articles 80. In other preferred embodiments, the concentration monitor 10 is not fixed to any particular position within the sterilization chamber 30, but is placed on or near the sterilized article 80 itself. In this way, the concentration monitor 10 can be used to measure the $H_2O_2$ concentration to which the sterilized article 80 is exposed. In particular, if the sterilized article 80 has a region which is exposed to a reduced concentration of $H_2O_2$ due to shadowing or a reduced opening, then the concentration monitor 10 can be placed within this region to ensure that a sufficient $H_2O_2$ concentration is maintained to sterilize this region. The small size of the concentration monitor of the present invention permits the concentration monitor to be placed in very restricted volumes, such as the inner volume of a lumen, or in a container or wrapped tray. In still other embodiments of the present invention, a plurality of concentration monitors 10 can be utilized to measure the $H_2O_2$ concentration at various positions of interest.

In certain embodiments, a reference temperature probe can be utilized to provide a measure of the ambient temperature within the sterilization chamber 30 to improve the performance of the concentration monitor 10. The temperature of the environment within the sterilization chamber 30 may fluctuate due to other factors unrelated to the hydrogen peroxide concentration. A reference temperature probe in close proximity to the $H_2O_2$ concentration monitor 10 can then be used to measure such non-$H_2O_2$-related temperature fluctuations and compensating for these non-$H_2O_2$-related temperature fluctuations from the temperature reading of the temperature probe of the $H_2O_2$ concentration monitor 10. Typically, the reference temperature probe is substantially identical to the $H_2O_2$ concentration monitor 10, but does not comprise the reactive chemical substance. For example, a PEG/acrylic $H_2O_2$ concentration monitor 10 can be paired with a reference temperature probe with the acrylic binder but without the PEG polymer. Alternatively, the $H_2O_2$ concentration monitor 10 can be paired with a bare reference temperature probe without the binder or the reactive chemical substance.

This invention may be embodied in other specific forms without departing from the essential characteristics as described herein. The embodiments described above are to be considered in all respects as illustrative only and not restrictive in any manner. The scope of the invention is indicated by the following claims rather than by the foregoing description. Any and all changes which come within the meaning and range of equivalency of the claims are to be considered within their scope.

What is claimed is:

1. An apparatus for monitoring the concentration of an oxidative gas or vapor, the apparatus comprising:
    a chemical substance which reacts non-catalytically with the oxidative gas or vapor to produce a heat change; and
    a temperature probe coupled to the chemical substance, wherein the temperature probe is adapted to respond to the heat change.

2. The apparatus as defined in claim 1, wherein the oxidative gas or vapor comprises hydrogen peroxide.

3. The apparatus as defined in claim 1, wherein the chemical substance is a material that is oxidized by hydrogen peroxide.

4. The apparatus as defined in claim 1, additionally comprising a carrier which couples the chemical substance to the temperature probe.

5. The apparatus as defined in claim 4, wherein the carrier comprises acrylic, epoxy, nylon, polyurethane, polyhydroxyethylenemethacrylate (polyHEMA), polymethylmethacrylate (PMMA), polyvinylpyrrolidone (PVP), polyvinylalcohol (PVA), silicone, tape, or vacuum grease.

6. The apparatus as defined in claim 4, wherein the carrier comprises a gas-permeable pouch or gas-impermeable enclosure with at least one hole.

7. The apparatus as defined in claim 6, wherein the gas-permeable pouch comprises a nonwoven polyolefin material.

8. The apparatus as defined in claim 1, wherein the apparatus further comprising a heat conductor between the chemical substance and the temperature probe.

9. The apparatus as defined in claim 1, wherein the temperature probe further comprising a connector to connect and disconnect the portion of the temperature probe coupled to the chemical substance to the remaining portion of the temperature probe.

10. The apparatus as defined in claim 1, wherein the temperature probe is movable and capable of measuring the temperature at a particular location, and producing an output signal which is a function of the temperature.

11. The apparatus as defined in claim 1, wherein the temperature probe is a fiberoptic temperature probe, fluoroptic temperature probe, thermocouple probe, thermistor, glass thermometer, RTD probe, temperature strip, optical temperature sensor, or infrared temperature sensor.

12. The apparatus as defined in claim 1, further comprising a reference temperature probe adapted to measure temperature fluctuations not due to the concentration of the oxidative gas or vapor.

13. The apparatus as defined in claim 12, wherein the reference temperature probe is in proximity to the temperature probe.

14. The apparatus as defined in claim 12, wherein the reference temperature probe is substantially identical to the temperature probe but does not comprise the chemical substance.

15. An apparatus for monitoring the concentration of an oxidative gas or vapor, the apparatus comprising:
    a chemical substance which reacts with the oxidative gas or vapor to produce a heat change, wherein the chemical substance comprises hydroxyl functional groups; and
    a temperature probe coupled to the chemical substance, wherein the temperature probe is adapted to respond to the heat change.

16. An apparatus for monitoring the concentration of an oxidative gas or vapor, the apparatus comprising:
    a chemical substance which reacts with the oxidative gas or vapor to produce a heat change, wherein the chemical substance is a material selected from the group consisting of magnesium chloride ($MgCl_2$), iron (II) acetate, potassium iodide (KI), sodium thiosulfate, molybdenum disulfide, 1,2-ethanedithiol, methyl disulfide, cysteine, methionine, and polysulfides; and
    a temperature probe coupled to the chemical substance, wherein the temperature probe is adapted to respond to the heat change.

17. An apparatus for monitoring the concentration of an oxidative gas or vapor, the apparatus comprising:
    a chemical substance which reacts with the oxidative gas or vapor to produce a heat change, wherein the chemical substance comprises a polymer comprising hydroxyl functional groups, the polymer being selected from the group consisting of polyethylene glycol (PEG), polyethylene oxide (PEO), and polyvinyl alcohol (PVA); and
    a temperature probe coupled to the chemical substance, wherein the temperature probe is adapted to respond to the heat change.

18. A method of monitoring the concentration of an oxidative gas or vapor, the method comprising:

providing a chemical substance which undergoes a non-catalytic reaction with the oxidative gas or vapor to be monitored, thereby producing a heat change;

providing a temperature probe coupled to the chemical substance, the temperature probe adapted to respond to the heat change produced by the reaction between the chemical substance and the oxidative gas or vapor to be monitored by producing an output signal which is a function of the concentration of the oxidative gas or vapor;

exposing the chemical substance to the oxidative gas or vapor;

measuring the output signal from the temperature probe; and determining the concentration of the oxidative gas or vapor based on the output signal.

19. The method as defined in claim 18, wherein the oxidative gas or vapor comprises hydrogen peroxide.

20. The method as defined in claim 18, wherein the chemical substance is a material that is oxidized by hydrogen peroxide.

21. The method as defined in claim 18, wherein the temperature probe is coupled to the chemical substance by a carrier comprising acrylic, epoxy, nylon, polyurethane, polyhydroxyethylenemethacrylate (polyHEMA), polymethylmethacrylate (PMMA), polyvinylpyrrolidone (PVP), polyvinylalcohol (PVA), silicone, tape, or vacuum grease.

22. The method as defined in claim 18, wherein the temperature probe is coupled to the chemical substance by a carrier comprising a gas-permeable pouch or gas-impermeable enclosure with at least one hole.

23. The method as defined in claim 18, additionally comprising moving the temperature probe to a particular location, and producing an output signal which is a function of the temperature at that location.

24. The method as defined in claim 18, additionally comprising:

providing a reference temperature probe which detects temperature fluctuations not due to the concentration of the oxidative gas or vapor and which produces a reference output signal which is a function of the temperature fluctuations;

measuring the reference output signal from the reference temperature probe; and utilizing the reference output signal to compensate for the temperature fluctuations not due to the concentration of the oxidative gas or vapor.

25. A method of monitoring the concentration of an oxidative gas or vapor, the method comprising:

providing a chemical substance which undergoes a reaction with the oxidative gas or vapor to be monitored, thereby producing a heat change, wherein the chemical substance comprises hydroxyl functional groups;

providing a temperature probe coupled to the chemical substance, the temperature probe adapted to respond to the heat change produced by the reaction between the chemical substance and the oxidative gas or vapor to be monitored by producing an output signal which is a function of the concentration of the oxidative gas or vapor;

exposing the chemical substance to the oxidative gas or vapor;

measuring the output signal from the temperature probe; and determining the concentration of the oxidative gas or vapor based on the output signal.

26. A method of monitoring the concentration of an oxidative gas or vapor, the method comprising:

providing a chemical substance which undergoes a reaction with the oxidative gas or vapor to be monitored, thereby producing a heat change, wherein the chemical substance is a material selected from the group consisting of magnesium chloride ($MgCl_2$), iron (II) acetate, potassium iodide (KI), sodium thiosulfate, molybdenum disulfide, 1,2-ethanedithiol, methyl disulfide, cysteine, methionine, and polysulfides;

providing a temperature probe coupled to the chemical substance, the temperature probe adapted to respond to the heat change produced by the reaction between the chemical substance and the oxidative gas or vapor to be monitored by producing an output signal which is a function of the concentration of the oxidative gas or vapor;

exposing the chemical substance to the oxidative gas or vapor;

measuring the output signal from the temperature probe; and determining the concentration of the oxidative gas or vapor based on the output signal.

27. A method of monitoring the concentration of an oxidative gas or vapor, the method comprising:

providing a chemical substance which undergoes a reaction with the oxidative gas or vapor to be monitored, thereby producing a heat change, wherein the chemical substance comprises a polymer comprising hydroxyl functional groups, the polymer being selected from the group consisting of polyethylene glycol (PEG), polyethylene oxide (PEO), and polyvinyl alcohol (PVA);

providing a temperature probe coupled to the chemical substance, the temperature probe adapted to respond to the heat change produced by the reaction between the chemical substance and the oxidative gas or vapor to be monitored by producing an output signal which is a function of the concentration of the oxidative gas or vapor;

exposing the chemical substance to the oxidative gas or vapor;

measuring the output signal from the temperature probe; and determining the concentration of the oxidative gas or vapor based on the output signal.

28. A sterilization system operated by a user, wherein the sterilization system comprises:

a chamber;

a door in the chamber;

a source of oxidative gas or vapor in fluid connection with the chamber;

a chemical concentration measuring system comprising at least one apparatus according to claim 1; and a control system which receives input from the chemical concentration measuring system to produce a desired concentration of said oxidative gas or vapor.

29. The system as defined in claim 28, wherein the system further comprises a pumping system to reduce the pressure in the chamber.

30. The system as defined in claim 28, wherein the oxidative gas or vapor comprises hydrogen peroxide.

31. The system as defined in claim 28, further comprising a reference temperature probe adapted to measure temperature fluctuations not due to the concentration of the oxidative gas or vapor.

* * * * *